United States Patent
Oka et al.

(10) Patent No.: US 11,147,750 B2
(45) Date of Patent: Oct. 19, 2021

(54) TWO-COMPONENT COSMETIC

(71) Applicant: SHISEIDO COMPANY, LTD., Tokyo (JP)

(72) Inventors: Takashi Oka, Yokohama (JP); Tomoaki Terada, Yokohama (JP); Ryo Furukawa, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 16/493,162

(22) PCT Filed: Mar. 6, 2018

(86) PCT No.: PCT/JP2018/008464
§ 371 (c)(1),
(2) Date: Sep. 11, 2019

(87) PCT Pub. No.: WO2018/168560
PCT Pub. Date: Sep. 20, 2018

(65) Prior Publication Data
US 2020/0069539 A1     Mar. 5, 2020

(30) Foreign Application Priority Data

Mar. 17, 2017 (JP) .............................. JP2017-052404
Sep. 29, 2017 (WO) .................. PCT/JP2017/035457

(51) Int. Cl.
*A61K 8/04*     (2006.01)
*A61K 8/19*     (2006.01)
*A61K 8/73*     (2006.01)
*A61Q 19/00*    (2006.01)

(52) U.S. Cl.
CPC ............... *A61K 8/042* (2013.01); *A61K 8/19* (2013.01); *A61K 8/733* (2013.01); *A61Q 19/00* (2013.01); *A61K 2800/10* (2013.01); *A61K 2800/88* (2013.01)

(58) Field of Classification Search
CPC ........................... A61K 8/733; A61K 2800/08
See application file for complete search history.

(56) References Cited

U.S. PATENT DOCUMENTS

2006/0198805 A1* 9/2006 Gupta .................. A61K 8/9711
424/70.13
2011/0081307 A1* 4/2011 Raineau ................. A61K 8/733
424/61

FOREIGN PATENT DOCUMENTS

| CN | 102920615 A | * | 2/2013 |
|---|---|---|---|
| JP | 55-127311 | | 10/1980 |
| JP | S55 127311 A | | 10/1980 |
| JP | 03-223213 | | 10/1991 |
| JP | 07-173032 | | 7/1995 |
| JP | 2002-114634 | | 4/2002 |
| JP | 2013-079203 | | 5/2013 |
| JP | 2013 079203 A | | 5/2013 |
| JP | B 5894791 | | 7/2013 |
| JP | A 6425710 | | 11/2018 |
| KR | 2012 0058917 A | | 6/2012 |
| KR | 2016 0005672 A | | 1/2016 |

OTHER PUBLICATIONS

Google patent search: kit calcium salt and alginate_May 4, 2020 (Year: 2020).*
Moisture barrier calcium gellan gum—Google Search Dec. 17, 2020 (Year: 2020).*
Moisture barrier calcium gellan gum—Google Patent Search Dec. 17, 2020 (Year: 2020).*
English translation of CN-102920615-A from EPO (Year: 2020).*
PCT/JP2018/008464 International Search Report (ISR) and Written Opinion (WO), dated Apr. 24, 2018, 3 pages—English, 7 pages—Japanese.
EP 18768275.2 Extended European Search Report dated Dec. 4, 2020, 10 pages—English.
Database WPI Week Sep. 2013 Nov. 2, 2012 Thomson Scientific, London, GB; AN 2012-092017, XP002801176, Joo Y A; Jung H.S.; Kim J.H.; Kim S K; Shin B M; "Gel-type cosmetic composition useful for sprying, comprises gelfan gum powder", 2 pages—English.
Li Xin et al.: "Nasal delivery of analgesic ketorolac tromethamine thermo and ion-sensitive in situ hydrogels", International Journal of Pharmaceutics, Elsevier, NL, vol. 489, No. 1, May 6, 2015, pp. 252-260, XP029183109, ISSN: 0378-5173, DOI: 10.1016/J.IJPHARM. 2015.05.009, abstract, introduction, 9 pages—English.

* cited by examiner

*Primary Examiner* — Michael P Cohen
(74) *Attorney, Agent, or Firm* — Andrew F. Young, Esq.; Nolte Lackenbach Siegel (57) ABSTRACT

The purpose of the present invention is to provide a two-component cosmetic which, when a first formulation and a second formulation are sequentially applied, forms a uniform gel film on the skin while imparting a feeling of moisture permeating the skin, thereby providing an ideal skin feel. The present invention pertains to a two-component cosmetic containing: (1) a first formulation containing a gel formation-promoting substance; and (2) a second formulation containing a gel-forming substance. The two-component cosmetic is characterized in that the first formulation is applied to the skin, and then the second formulation is applied thereto.

3 Claims, 4 Drawing Sheets

TWO-COMPONENT COSMETIC

CROSS REFERENCE TO RELATED APPLICATIONS

This application relates to, and claims priority as a § 371 national phase, from PCT/JP2018/008464 filed Mar. 6, 2018, the entire contents of which are incorporated herein by reference, which in turn claims priority from PCT SN PCT/JP2017/035457 filed Sep. 29, 2017 and from JP Ser. No.: 2017-052404 filed Mar. 17, 2017.

FIGURE SELECTED FOR PUBLICATION

FIG. 1

TECHNICAL FIELD

The present invention relates to a two-component cosmetic (two preparations for one cosmetic). More specifically, the present invention relates to a cosmetic functionable by applying two components (as preparations), for example, one application on skin followed by another application over the same skin (in series), by which a uniform (homogeneous) gel film is formed and as a result, fresh elasticity to the skin is provided and moist feeling becomes long-lasting.

BACKGROUND ART

While ideal skin feels are different among persons, such feels are often expressed by, for example, fine, refined and smooth, resilient and elastic, moisturized and moist feeling, and/or springy and tight-fitting feeling skin textures in touch with hand. If moisture in the skin is lost by, for example, an external stimulus such as drying of ambient air or ultraviolet light, or aging, elasticity of the skin is lost and is roughened, and the skin is farther away from an ideal skin feeling. Accordingly, a cosmetic which enables the above ideal skin feels to be actually felt can also give the psychological effects, for example, provide positive emotions, and youthful and cheerful emotions to users.

Cosmetics having a form called jelly or gel are known as skincare cosmetics which are uniform in appearance and are transparent to translucent, and which provide fresh feeling. In particular, aqueous gel includes a large amount of moisture, and thus is effective as a cosmetic base material providing the effects of replenishing moisture to the skin, moisturizing of the skin, and refreshing of the skin (Non-Patent Document 1).

Such aqueous gel often utilizes a thickening function of a water-soluble polymer typified by a carboxy vinyl polymer or methylcellulose, and various cosmetic ingredients are added to a base material including a water-soluble polymer (Non-Patent Document 1 and Patent Document 1).

Patent Document 1 proposes a gel-like skin external preparation which provides no sticky feeling in application, which has a flexible film feeling, which is excellent in retention ability of a moisturizing feeling, and which is favorable in storage stability. The gel-like cosmetic includes (A) phospholipid, (B) a carboxy vinyl polymer and/or a salt thereof, and an acrylic acid/alkyl methacrylate copolymer (a mass ratio of the carboxy vinyl polymer to the acrylic acid/alkyl methacrylate copolymer of 5:1 to 1:1), (C) a fatty acid ester of cholesterol or phytosterol, and (D) a saturated monohydric alcohol having 1 to 3 carbon atoms. The cosmetic of Patent Document 1, however, fails to provide any sufficient retention ability of moisturizing when (A) the phospholipid and (C) the cholesterol or phytosterol, which are considered not directly related to gel formation, are omitted (see, Comparative Examples 1 and 3).

On the other hand, there is also a cosmetic including two components (preparations), one component containing a gel-forming substance and the other component containing a substance for promoting gelation of the gel-forming substance, which allows gel to be formed on the skin. In such a conventional two-component cosmetic, however, a first component to be first applied contains a gel-forming substance and a second component to be subsequently applied contains a gelling promotion substance.

For example, Patent Document 2 discloses a cosmetic including a combination of a first component including at least one reactive gelling agent selected from the group consisting of kappa carrageenan, alginate and pectin, and a second component including a cation for promotion of gelling of the gelling agent, wherein gelling of the first component occurs by applying the first component to a portion to be adhered and then applying the second component.

However, when such a first component containing water-soluble polymer(s) such as kappa carrageenan, alginate and/or pectin and having a viscosity of 100 to 40000 cP is directly applied on bare skin, the first component may not spread evenly thereon.

Patent Document 2 also discloses a gelled film formed by application of the second component, but such a gelled film is a hard film based on sodium alginate, which is to be peeled as a peel-off type pack cosmetic (peel-off pack cosmetic), and thus such a gelled film by itself is insufficient in the effect of closing (holding) moisture on the skin surface (hereinafter, also referred to as "occlusion effect"). Much the same is true on peel-off pack cosmetics based on sodium alginate and PVA, described in Patent Documents 3 and 4.

CITATION LIST

Patent Documents

Patent Document 1: JP-B 5894791
Patent Document 2: JP-A Sho 64-25710
Patent Document 3: JP-A 2002-114634
Patent Document 4: JP-A Sho 55-127311

Non-Patent Document

Non-Patent Document 1: Takeo MITSUI, "New Cosmetic Science", second edition, pages 380 to 381, issued by Nanzando Co., Ltd., on Jan. 18, 2001

SUMMARY OF INVENTION

Technical Problem

Accordingly, an object of the present invention is to provide a two-component type cosmetic (i.e. two preparations for one cosmetic) which not only provides a moisture penetration feeling to the skin, but also allows an ideal skin feeling to be realized, by formation of a uniform (homogeneous) gel film on the skin due to continuous application of a first component and a second component.

Solution to Problem

The present inventors have made intensive studies in order to solve the above problems, and as a result, have found a novel cosmetic which can solve the above problems, in which a first component to be first applied contains no gel-forming substance but contains a gel formation promoting substance and a second component to be subsequently applied contains a gel-forming substance and the first component and the second component are applied sequentially, thereby leading to completion of the present invention.

That is, the present invention provides a two-component cosmetic comprising:

(1) a first component that comprises a substance that promotes a gel formation; and (2) a second component that comprises a substance that forms a gel; wherein the first component is first applied to a skin and next, the second component is applied to the first component on the skin.

Advantageous Effects of Invention

The two-component cosmetic of the present invention is as follows: a first component to be first applied does not include any gel-forming substance such as a water-soluble polymer and is low in viscosity and thus is excellent in moisture penetration feeling to the skin, and a second component to be applied in the presence of the first component on the skin is uniformly spread to allow a gel-forming substance included in the second component to be brought into contact with a gel formation promoting substance included in the first component and thus be gelled to thereby form a uniform gel film on the skin, thereby enabling moisture to be retained on the skin and, as a result, enabling an ideal skin feeling to be realized.

DESCRIPTION OF EMBODIMENTS

The two-component cosmetic of the present invention includes (1) a first component containing a gel formation promoting substance and (2) a second component containing a gel-forming substance.

The "gel-forming substance" in the present invention means a substance which can be brought into contact with the "gel formation promoting substance" to thereby form gel. For example, "the state where a large amount of a solvent is included in a polymer network" is called "gel" in the cosmetic field (Japanese Patent Office, "Standard Techniques", "Perfume", 2007). Such gel can be classified to hydrogel with water as a solvent, oil gel with an organic solvent as a solvent, and xerogel with gas as a solvent. The gel in the present invention is preferably hydrogel (polymer hydrogel).

The "polymer hydrogel" can be defined as gel which has a three-dimensional network structure (polymer network) formed by mutual connection of a plurality of polymers at crosslinking points, and which includes water or an aqueous medium as a solvent.

A mechanism for gel formation by a polymer is considered to involve forming a network structure by mere entanglement of polymer chains or forming a network structure by partial binding (crosslinking) of polymer chains. Examples of factors for crosslinking of polymer chains include a covalent bond, an ionic bond, a coordination bond and a hydrogen bond by a crosslinking agent. Gel is then classified to chemical gel and physical gel depending on the crosslinking system (for example, Fumihiko TANAKA, "Polymer Physics", pages 91 to 97, issued by Shokabo, 2004,). The chemical gel refers to gel where a crosslinking point is formed by a covalent bond, and the physical gel refers to gel where crosslinking is formed by an ionic bond, a coordination bond, a hydrogen bond, or any intermolecular interaction such as an electrostatic force.

The gel in the present invention is crosslinked gel, preferably physical gel, and is desirably obtained by an ionic bond, a coordination bond, or a hydrogen bond as a crosslinking factor (gelling factor). That is, the gel in the present invention is gel obtained by gelling due to formation of crosslinking by mixing the first component and the second component, thus is in the state of being a gel dispersion where gelling partially progresses in macroscopic observation of a mixture, and is applied to thereby provide a uniform gel film.

The "gel" is herein defined as the above-defined polymer hydrogel (preferably physical gel) in which crosslinking is formed by mixing of the first component and the second component and the viscosity as measured according to the following measurement method is 400 cps or more.

(Measurement Method)

25 g of the first component and 25 g of the second component are weighed and placed in a 100-mL container, and mixed by use of a handy mixer for 10 seconds and then transferred to a 50-mL container, and the viscosity is measured by use of a B-type viscometer at 30° C.

While "gel", "jelly", and the like are used as terms expressing the form of a cosmetic product, one satisfying the above viscosity condition is encompassed in the "gel" in the present invention.

It, however, goes without saying that a system where no crosslinking is formed by mixing of the first component and the second component, for example, a system where the first component is water and the second component is an aqueous water-soluble polymer solution (chemical gel) are not encompassed in the "gel" in the present invention even in the case where a mixture of both the components has a viscosity of 400 cps or more.

The "substance that forms a gel (gel-forming substance)" in the present invention is a substance which is to be brought into contact with the "substance that promotes a gel formation (gel formation promoting substance)" described below and thus gelled. A representative example of a gel-forming substance for formation of a hydrogel is a water-soluble polymer which is a substance serving as a main agent of a network structure for gelling.

The water-soluble polymer preferably used in the present invention is not particularly limited, and is selected from a synthetic or natural water-soluble polymer which can be used for cosmetics and which can interact with a gel formation promoting substance to thereby form a crosslinking point and thus form a three-dimensional network structure.

Specific examples include a carboxy vinyl polymer, a (meth)acrylic acid polymer, gellan gum, alginic acid, carrageenan, pectin, xanthan gum, locust bean gum, and tamarind seed gum.

The "gel formation promoting substance" in the present invention is a substance which generates gelling of the gel-forming substance. That is, in the case where the gel-forming substance is a water-soluble polymer, the substance is a substance which can form a crosslinking point for binding of the polymer chain.

For example, in the case where the water-soluble polymer is a polymer having a carboxyl group, such as a carboxy vinyl polymer or a (meth)acrylic acid polymer, the gel formation promoting substance is a substance which can allow for crosslinking by a hydrogen bond or an ionic bond, for example, polyethylene glycol or a di- or higher valent cation.

In the case where the gel-forming substance (water-soluble polymer) is gellan gum, alginic acid, carrageenan, or LM pectin, the gel formation promoting substance is a cationic substance such as a metal ion. The metal ion is preferably a metal cation selected from the group consisting of $Na^+$, $K^+$, $Ca^{2+}$, $Mg^{2+}$ and $Al^{3+}$, and among them, particularly preferably a mono- or divalent metal cation.

Such a metal cation is not particularly limited in terms of the source thereof, and can be contained in the form of halide, nitrate, sulfate, lactate, or the like. Such a metal cation, which is contained in the first component, in the form of a salt type agent such as Na 4-methoxysalicylate, and which is released from the salt type agent, can also be adopted as the gel formation promoting substance. The salt type agent here used is not particularly limited as long as it is a water-soluble agent which can be taken together with the metal cation to form a salt and which can be usually contained in a cosmetic or the like. Examples include salts of L-ascorbic acid and a derivative thereof, salts of tranexamic acid and a derivative thereof, salts of alkoxysalicylic acid and a derivative thereof, and salts of glutathione and a derivative thereof.

Examples of the L-ascorbic acid derivative include L-ascorbic acid monoesters such as L-ascorbic acid monophosphate and L-ascorbic acid-2-sulfate; L-ascorbic acid triesters such as L-ascorbic acid triphosphate; and L-ascorbic acid glucosides such as L-ascorbic acid2-glucoside.

Examples of the tranexamic acid derivative include dimers of tranexamic acid (for example, trans-4-(trans-aminomethylcyclohexanecarbonyl)aminomethylcyclo-hexanecarboxylic acid hydrochloride), esters of tranexamic acid and hydroquinone (for example, 4-(trans-aminomethylcyclohexanecarboxylic acid 4'-hydroxyphenyl ester), esters of tranexamic acid and gentisic acid (for example, 2-(trans-4-aminomethylcyclohexylcarbonyloxy)-5-hydroxybenzoic acid), and amides of tranexamic acid (for example, trans-4-aminomethylcyclohexanecarboxylic acid methylamide, trans-4-(p-methoxybenzoyl)aminomethylcyclohexanecarboxylic acid, and trans-4-guanidinomethylcyclohexanecarboxylic acid).

Alkoxysalicylic acid is obtained by substituting any hydrogen atom of salicylic acid at the 3-, 4-, or 5-position with an alkoxy group, and such an alkoxy group as a substituent is preferably any of a methoxy group, an ethoxy group, a propoxy group, an isopropoxy group, a butoxy group, and an isobutoxy group, further preferably a methoxy group or an ethoxy group. Specific examples include 3-methoxysalicylic acid, 3-ethoxysalicylic acid, 4-methoxysalicylic acid, 4-ethoxysalicylic acid, 4-propoxysalicylic acid, 4-isopropoxysalicylic acid, 4-butoxysalicylic acid, 5-methoxysalicylic acid, 5-ethoxysalicylic acid, and 5-propoxysalicylic acid.

The salt of the salt type agent described above is not particularly limited, and examples include not only alkali metal salts or alkali earth metal salts such as a sodium salt, a potassium salt, a calcium salt, and a magnesium salt, but also salts such as an ammonium salt and an amino acid salt.

A polysaccharide polymer such as gellan gum or carrageenan is considered to be gelled by forming a spiral structure from each polysaccharide polymer randomly present and then forming steric network structure and binding region.

The content of gellan gum as the gel-forming substance of the second component is preferably 0.1 to 1.0% by mass, more preferably 0.2 to 0.7% by mass, and the content of the cationic substance as the gel formation promoting substance of the first component is preferably 0.01 to 3% by mass, more preferably 0.05 to 1% by mass, from the viewpoint that favorable gel formation and an excellent occlusion effect are achieved.

While alginic acid by itself is insoluble in water, an alkali metal salt such as a sodium salt, an ammonium salt, an organic amine salt, and the like (hereinafter "sodium salt and the like") are soluble in water. Sodium alginate or the like in an aqueous solution, which is dissociated as an alginic acid ion, generates calcium alginate by addition of any ion of a divalent metal (alkali earth metal) such as calcium or magnesium, thereby allowing for the occurrence of gelling. That is, it is considered that such a divalent metal ion promotes association of alginic acid molecules to form a steric structure, and a structure where such an ion serves as a bridge to bind molecules is called egg-box.

The content of sodium alginate in the second component is preferably 0.1 to 5% by mass, more preferably 0.3 to 2% by mass, and the content of the cationic substance (calcium salt) as the gel formation promoting substance in the first component is preferably 0.1 to 5% by mass, from the viewpoint that favorable gel formation and an excellent occlusion effect are achieved.

In the case where the gel-forming substance (water-soluble polymer) is xanthan gum, the gel formation promoting substance can be locust bean gum, or, on the contrary, a case can also be adopted where the gel-forming substance is locust bean gum and the gel formation promoting substance is xanthan gum. It is considered that such a system allows for gel formation due to intermolecular interaction.

The ratio (weight ratio) of the contents of xanthan gum to locust beam gum is preferably 2:8 to 8:2, more preferably 4:6 to 6:4, from the viewpoint that favorable gel formation and an excellent occlusion effect are achieved.

In the case where the gel-forming substance (water-soluble polymer) is tamarind seed gum, it is considered that a reduction in moisture activity due to the presence of a sugar or an alcohol as the gel formation promoting substance and a reduction in electric repulsion in an acidic condition with an acid allow gelling to occur due to association of molecules by a hydrogen bond. The gel formation promoting substance is suitably ethanol, concentrated glycerin, 1,3-butylene glycol, dipropylene glycol, sorbit, or the like, and the content of such each substance is preferably 5 to 35% by mass, more preferably 10 to 30% by mass.

The pectin for use as the gel-forming substance (water-soluble polymer) is classified to HM (high methoxylated) pectin having a degree of esterification of 50% or more and LM (low methoxylated) pectin having a degree of esterification of less than 50%, and the gel formation promoting substance corresponding to HM pectin is an acid and the gel formation promoting substance corresponding to LM pectin is a divalent metal ion such as a calcium ion.

The first component in the two-component cosmetic of the present invention contains the gel formation promoting substance and is preferably formulated to include no gel-forming substance so that no gelling occurs before application to the skin. On the contrary, the second component is preferably formulated not to contain any substance for promotion of gelling of the gel-forming substance contained, for example, a metal ion.

The two-component cosmetic of the present invention is preferably in the form of an aqueous composition including the first component and the second component. An aqueous composition means a composition which includes 50% by mass or more of an aqueous cosmetic ingredient based on the total weight of the composition and which is in the form of an aqueous solution, an oil-in-water emulsion, or the like.

The two-component cosmetic of the present invention allows an ideal skin feeling to be realized by applying (1) a first component containing a gel formation promoting substance, to the skin, and then applying (2) a second component containing a gel-forming substance, onto the first component, thereby imparting moist feeling and elasticity to the skin.

The first component is usually applied to the skin immediately after washing, to impart a fresh moist feeling, and thus is preferably in the form of a composition having a low viscosity (for example, 100 mPa·s or less), for example, a lotion or an emulsion. A cosmetic ingredient which increases a penetration feeling to the skin and improves comfortability to the skin is also preferably contained therein. Accordingly, the first component preferably contains a moisturizing agent, a lower alcohol, an oil content, a surfactant, and the like. On the other hand, it is preferable that a film forming agent such as polyvinyl alcohol is not contained or the content thereof is minimized (for example, about 1% by mass or less).

The moisturizing agent may be any ingredient applicable for skincare cosmetics and the like, and examples include polyhydric alcohols such as glycerin, dipropylene glycol, 1,3-butylene glycol and polyethylene glycol, sugars such as erythritol, trehalose and sorbitol, and polysaccharides such as hyaluronic acid.

The oil content is polar oil, non-polar oil, silicone oil, or the like, and examples include polar oil such as glyceryl tri-2-ethylhexanoate, non-polar oil such as an α-olefin oligomer, and silicone oil such as methylpolysiloxane.

The surfactant which can be contained is a nonionic surfactant, an ionic surfactant, an amphoteric surfactant, or the like, and examples include nonionic surfactants such as polyoxyethylene hydrogenated castor oil, ionic surfactants such as N-stearoyl-N-methyl taurine sodium, and amphoteric surfactants such as N-lauryldimethylaminoacetic acid betaine.

The second component that is applied onto the skin to which the first component is applied, forms a gel film on the skin to impart tension, elasticity, plump feeling, and the like. The form of the second component is not particularly limited, and the second component can be in the form of a composition having viscous properties depending on the application form (for example, a viscosity of about 1 to 100,000 mPa·s, preferably 1 to 10,000 mPa·s), for example, a mist lotion, an emulsion or a cream. The second component may contain a film forming agent, such as polyvinyl alcohol, which can impart tension feeling. Furthermore, the second component may contain a moisturizing agent for enhancing moisturization effect, an oily ingredient for supplying the skin with an oil content, and also the surfactant together. A thickener for adjusting the viscosity of the second component may also be additionally contained.

The moisturizing agent may be any applicable agent for skincare cosmetics and the like, and examples include polyhydric alcohols such as glycerin, dipropylene glycol (DPG), 1,3-butylene glycol (BG) and polyethylene glycol, sugars such as erythritol, trehalose and sorbitol, and polysaccharides such as hyaluronic acid.

The oily ingredient (oil content) is polar oil, non-polar oil, silicone oil, or the like, and examples include polar oil such as glyceryl tri-2-ethylhexanoate, non-polar oil such as an α-olefin oligomer, and silicone oil such as methylpolysiloxane.

It is noted that, even if the content of the gel-forming substance in the entire preparation is constant, an increase in the content of the oil content in the preparation may naturally decrease the amount of moisture, resulting in an increase in the concentration of the gel-forming substance in an aqueous phase and progression of gelling to thereby cause a hard film to be formed. Thus, the amount of the oil content contained, such as non-volatile hydrocarbon oil (for example, liquid paraffin), is preferably less than 15% by mass, more preferably less than 10% by mass, further preferably less than 5% by mass.

The surfactant which can be contained is a nonionic surfactant, an ionic surfactant, an amphoteric surfactant, or the like, and examples include nonionic surfactants such as polyoxyethylene hydrogenated castor oil, ionic surfactants such as N-stearoyl-N-methyl taurine sodium, and amphoteric surfactants such as N-lauryldimethylaminoacetic acid betaine.

The two-component cosmetic of the present invention is particularly suitable as a skin-care cosmetic which enables an ideal skin feel to be actually felt by spreading the first component and then spreading the second component, but is not limited thereto and can also be provided as a sun-care cosmetic, a haircare cosmetic, a makeup cosmetic, or the like which is excellent in moisture retention (occlusion effect).

Any other ingredient which a cosmetic, in particular, a skincare cosmetic or the like can contain may be arbitrarily contained in the two-component cosmetic of the present invention as long as the effect of the present invention is not impaired. Examples of such any other ingredient include an antioxidant, a preservative agent, an ultraviolet absorber, a powdery ingredient, and various agents (skin-whitening agent, skin quality improver, and the like), but are not limited thereto.

The forms of the containers and the application forms of the first component and the second component are not particularly limited. For example, a common form of a cosmetic container, such as a dispenser container, an aerosol container, or a jar container can be arbitrarily adopted. Any application form (application method) can also be adopted, for example, common application by hand (application by fingers), application by cotton, or spraying by mist or the like.

EXAMPLES

Hereinafter, the present invention will be described in more detail with reference to Examples, but the present invention is not intended to be limited to such Examples at all. The content of any ingredient is expressed by "% by mass" based on the total amount of any composition in which such an ingredient is contained, unless specifically noted.

(Example 1)

A first component (lotion) was prepared in a formulation presented in Table 1 below, and a second component (emulsion) was prepared in a formulation presented in Table 2 below.

TABLE 1

| Ingredient | Content (%) |
| --- | --- |
| Ion exchanged water | Balance |
| Ethanol | 7 |
| Concentrated glycerin | 8 |
| Dipropylene glycol | 7 |
| 1,3-Butylene glycol | 4 |
| Polyoxyethylene methyl glucoside | 0.5 |
| Polyethylene glycol 1000 | 1 |
| Erythritol | 0.1 |
| Trehalose | 1 |
| Magnesium chloride | 0.03 |
| Sodium chloride | 1 |
| Polyoxyethylene (14) polyoxypropylene (7) dimethyl ether | 3 |
| Polyoxyethylene polyoxypropylene 2-diethyl tetradecyl ether | 0.2 |
| Sodium lactate | 0.4 |
| Trisodium ethylenediaminetetraacetate | 0.03 |
| Phenoxyethanol | 0.5 |
| Perfume | q.s. |
| Total | 100 |

TABLE 2

| Ingredient | Content (%) |
| --- | --- |
| Ion exchanged water | Balance |
| Ethanol | 2 |
| Concentrated glycerin | 4 |
| Dipropylene glycol | 5 |
| Polyvinyl alcohol | 0.1 |
| Polyoxyethylene hydrogenated castor oil (60E.O.) | 0.1 |
| Acrylic acid/alkyl methacrylate copolymer | 0.05 |
| Carboxy vinyl polymer | 0.1 |
| Xanthan gum | 0.05 |
| Gellan gum | 0.4 |
| Potassium hydroxide | 0.05 |
| α-Olefin oligomer | 3 |
| Pentaerythrityl tetra2-ethylhexanoate | 1 |
| Macadamia nut oil fatty acid phytosteryl | 0.3 |
| Di(phytosteryl/2-octyldodecyl) N-lauroyl-L-glutamate | 1 |
| Polybutene | 1 |
| Phenoxyethanol | 0.5 |
| Sodium metaphosphate | 0.03 |
| Perfume | q.s. |
| Total | 100 |

The first component and the second component were applied to evaluate the ability of retention of moisture on the skin surface (occlusion ability) and the surface roughness of a formed gel film, with respect to the respective applications when (1) the first component was first applied and next, the second component, (2) the second component was first applied and next, the first component, and case (3) the first component and the second component were pre-mixed in advance and the resulting mixture was applied.

<Evaluation of Occlusion Ability>

(1) A paper filter to which the first component is first applied and then the second component is applied (Paper Sample (1)), (2) a paper filter to which the second component is first applied and then the first component is applied (Paper Sample (2)), and (3) a paper filter to which a mixture, prepared in advance, of the first component and the second component is applied (Paper Sample (3)), were prepared (each component amount: 5 µL/cm$^2$). Each of the paper filters was sandwiched between a vial bottle charged with a constant amount of water and a punctured lid, and the evaporation amount of moisture was measured over time to evaluate the occlusion ability based on the amount of moisture decreased. The results are illustrated in FIG. 1 (the results with respect to a paper filter with no application, as a control, are also illustrated).

Figure 1:
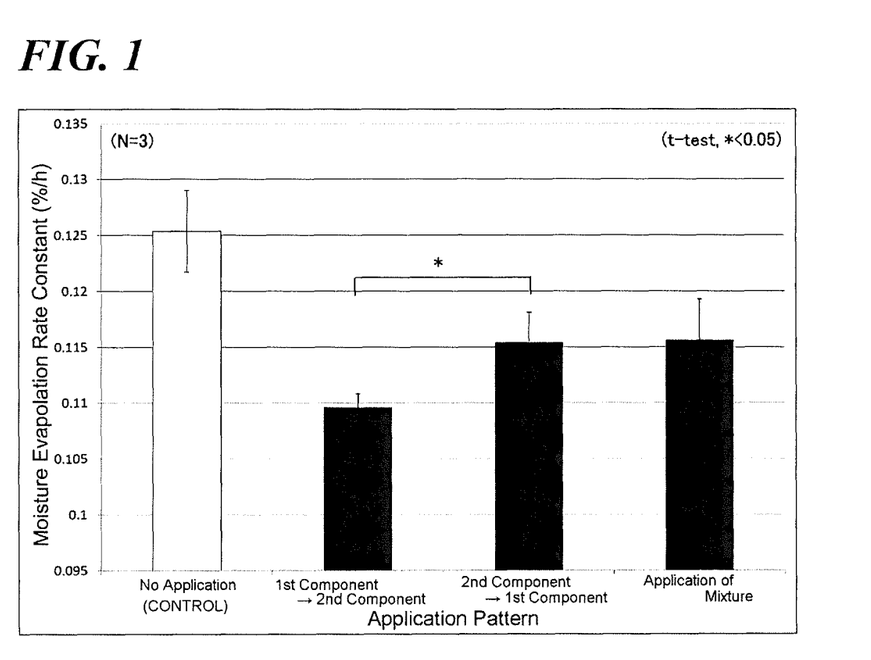
FIG. 1 is a graph illustrating comparison of the occlusion effect in Example 1.

It was revealed from the results represented in FIG. 1 that the moisture evaporation rate constant of the filter paper (Paper Sample (1)), to which the first component was first applied and then the second component was applied, was significantly low in comparison with those of the filter paper (Paper Sample (2)), to which the two components were applied in reverse order, and the filter paper (Paper sample (3)), to which the pre-mixture was applied as one component. These results indicate that the filter paper (Paper Sample (1)), to which the first component was first applied and then the second component was applied, has an extremely high occlusion ability.

<Evaluation of Smoothness of Applied Film>

Each of applied films, (1) an applied film obtained by application of the first component and then application of the second component (Film Sample (1)), (2) an applied film obtained by application of the second component and then application of the first component (Film Sample (2)), and (3) an applied film obtained by application of a sample obtained by pre-mixture of the first component and the second component in advance (Film Sample (1)), was produced on a glass plate by use of a doctor blade (75 µm), and dried at room temperature overnight, and the surface roughness Ra was measured using a laser microscope. The results are illustrated in FIG. 2.

Figure 2:
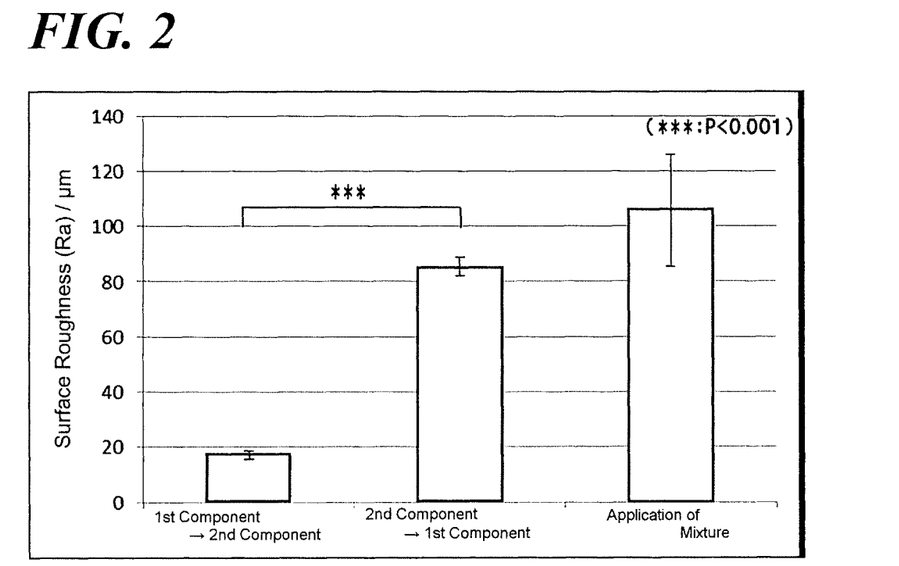
FIG. 2 is a graph illustrating comparison of the surface roughness of an applied film in Example 1.

As illustrated in FIG. 2, (1) the applied film obtained by application of the first component and then application of the second component (Film Sample (1)) was significantly reduced in Ra as compared with other applied films (Film Samples (2) and (3)). It was thus supposed that a smooth applied film was formed and thus was excellent in occlusion effect.

<Usability Test>

The skin texture after first application of the first component and subsequent application of the second component was evaluated according to sensory evaluation by twelve healthy female panelists and was rated according to the following criteria.

Figure 3:
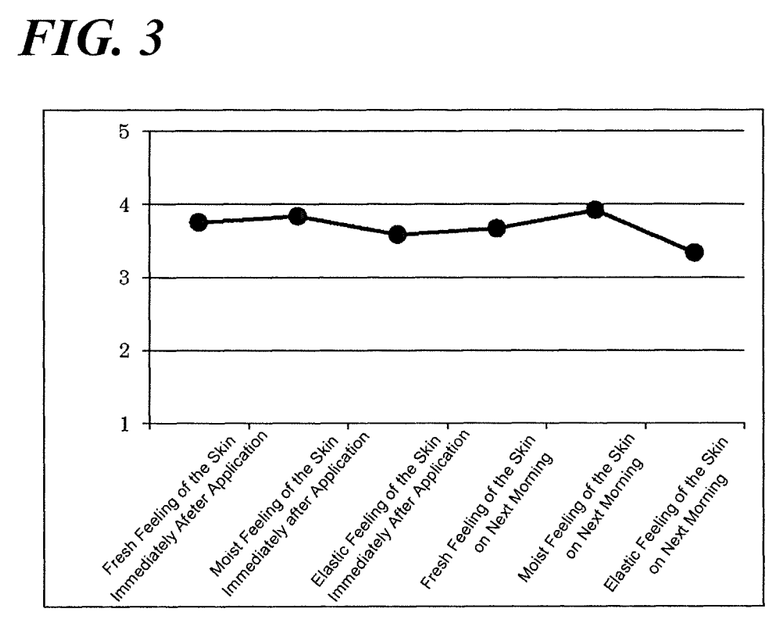
FIG. 3 is a graph illustrating the results of a usability test in Example 1.

5: very excellent skin texture
4: excellent skin texture
3: moderate
2: no excellent skin texture
1: no excellent skin texture at all The rating results obtained (average value at N=12) are illustrated in FIG. 3. As clear from the results in FIG. 3, it was confirmed that the two-component cosmetic of the present invention was used to thereby allow skin textures excellent in freshness, moisturized feeling and elastic feeling to be sustained not only immediately after application, but also in the next morning after application, and could impart ideal skin feelings.

(Example 2)

A first component (lotion) was prepared in a formulation presented in Table 3 below, and a second component (emulsion) was prepared in a formulation presented in Table 4 below.

TABLE 3

| Ingredient | Content (%) |
| --- | --- |
| Ion exchanged water | Balance |
| Concentrated glycerin | 4 |
| 1,3-Butylene glycol | 7 |
| Dipropylene glycol | 4 |

TABLE 3-continued

| Ingredient | Content (%) |
|---|---|
| Polyoxyethylene (14) polyoxypropylene (7) dimethyl ether | 1 |
| Carboxymethylcellulose sodium | 0.1 |
| Polyoxyethylene hydrogenated castor oil | 0.15 |
| Polyglyceryl diisostearate | 0.1 |
| Poly(oxyethylene/oxypropylene) methylpolysiloxane copolymer | 0.5 |
| Isostearyl alcohol | 0.2 |
| Methylphenylpolysiloxane | 0.15 |
| Magnesium chloride | 0.1 |
| Calcium chloride | 0.2 |
| Lactic acid | 0.04 |
| Sodium lactate | 0.35 |
| Sodium metaphosphate | 0.01 |
| Phenoxyethanol | 0.5 |
| Perfume | q.s. |
| Total | 100 |

TABLE 4

| Ingredient | Content (%) |
|---|---|
| Ion exchanged water | Balance |
| Ethanol | 1.5 |
| Concentrated glycerin | 5 |
| Dipropylene glycol | 3 |
| Diglycerin | 0.3 |
| Xylitol | 0.2 |
| Polyoxyethylene (17) polyoxypropylene (4) dimethyl ether | 0.2 |
| Gellan gum | 0.5 |
| Potassium hydroxide | 0.02 |
| Polyoxyethylene glyceryl isostearate | 0.3 |
| Polyoxyethylene/methylpolysiloxane copolymer | 0.3 |
| Behenyl alcohol | 2 |
| Batyl alcohol | 0.6 |
| Behenic acid | 0.2 |
| Glyceryl tri-2-ethylhexanoate | 1 |
| Di(phytosteryl/2-octyldodecyl) N-lauroyl-L-glutamate | 0.1 |
| Myristyl myristate | 0.2 |
| Methylphenylpolysiloxane | 1 |
| Methylpolysiloxane | 3 |
| Citric acid | 0.01 |
| Sodium citrate | 0.04 |
| Disodium edetate | 0.01 |
| Phenoxyethanol | 0.4 |
| Methylparaben | 0.1 |
| Perfume | q.s. |
| Total | 100 |

The first component described in Table 3 and the second component described in Table 4 were used to evaluate the ability of retention of moisture on the skin surface (occlusion ability) by the same method as in Example 1, with respect to a filter paper (1) to which only the first component was applied, a filter paper (2) to which a pre-mixture of the first component and the second component in advance was applied, and a filter paper (3) to which the first component was first applied and the second component was then applied. The results are illustrated in FIG. 4.

Figure 4:
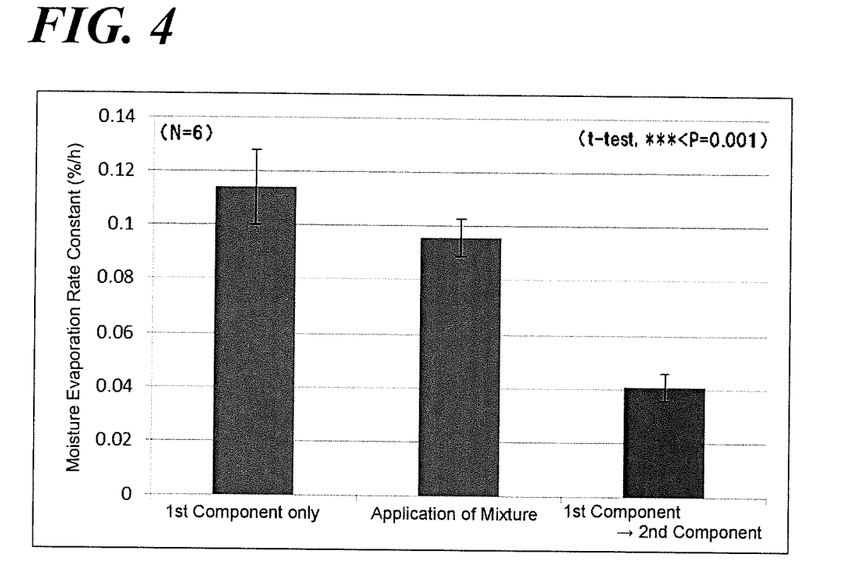
FIG. 4 is a graph illustrating comparison of the occlusion effect in Example 2.

It was confirmed from the results illustrated in FIG. 4 that the filter paper (3) of application of the first component and the application of the second component provided a significantly low moisture evaporation rate constant and an extremely high occlusion ability as compared with other two filter papers (1) and (2).

(Example 3)

A first component (lotion) was prepared in a formulation presented in Table 5 below, and a second component (emulsion) was prepared in a formulation presented in Table 6 below.

TABLE 5

| Ingredient | Content (%) |
|---|---|
| Ion exchanged water | Balance |
| Ethanol | 7 |
| Concentrated glycerin | 8 |
| 1,3-Butylene glycol | 4 |
| Polyoxyethylene methyl glucoside | 0.2 |
| Polyethylene glycol 1500 | 1 |
| Erythritol | 0.05 |
| Trehalose | 0.5 |
| Magnesium chloride | 0.02 |
| Calcium chloride | 0.02 |
| Sodium chloride | 0.5 |
| Polyoxyethylene (14) polyoxypropylene (7) dimethyl ether | 3 |
| Polyoxyethylene polyoxypropylene decyl tetradecyl ether | 0.2 |
| Sodium lactate | 0.1 |
| Trisodium edetate | 0.02 |
| Phenoxyethanol | 0.5 |
| Perfume | q.s. |
| Total | 100 |

TABLE 6

| Ingredient | Content (%) |
|---|---|
| Ion exchanged water | Balance |
| Ethanol | 5 |
| Concentrated glycerin | 6 |
| 1,3-Butylene glycol | 6 |
| Xanthan gum | 0.2 |
| Hydrophobically modified alkyl cellulose | 0.1 |
| Gellan gum | 0.4 |
| Polyoxyethylene behenyl ether | 1 |
| PEG/PPG-14/7-dimethyl ether | 2 |
| Behenyl alcohol | 1 |
| Stearyl alcohol | 0.2 |
| Caprylyl methicone | 5 |
| Methylpolysiloxane | 2 |
| Decamethyltetrasiloxane | 10 |
| Isostearic acid | 0.1 |
| Octyl methoxycinnamate | 3 |
| Octocrylene | 5 |
| Oxybenzone | 2 |
| Citric acid | 0.05 |
| Sodium citrate | 0.15 |
| Disodium edetate | 0.1 |
| Hydrophobized zinc oxide | 10 |
| Total | 100 |

The first component and the second component described in Tables 5 and 6 were used to evaluate the ability of retention of moisture on the skin surface (occlusion ability) by the same method as in Example 2.

As a result, it could be confirmed, as in Example 2, that the filter paper (3) of application of the first component and the application of the second component provided a significantly low moisture evaporation rate constant and an extremely high occlusion ability as compared with other two filter papers (1) and (2).

(Example 4)

A second component (lotion) having a low viscosity was prepared in a formulation presented in Table 7 below. When the second component is paired with the first component (lotion) described in Table 1, 3 or 5, both of the first component and the second component of the resultant two-component cosmetic become applicable by spraying as a mist.

TABLE 7

| Ingredient | Content (%) |
| --- | --- |
| Ion exchanged water | Balance |
| Concentrated glycerin | 4 |
| Diglycerin | 1 |
| Dipropylene glycol | 6 |
| Trehalose | 3 |
| Gellan gum | 0.5 |
| Disodium edetate | 0.01 |
| Phenoxyethanol | 0.4 |
| Citric acid | 0.01 |
| Sodium citrate | 0.04 |
| Total | 100 |

(Example 5)

A first component (lotion) was prepared in a formulation presented in Table 8 below, and a second component (lotion) was prepared in a formulation presented in Table 9 below.

TABLE 8

| Ingredient | Content (%) |
| --- | --- |
| Water | Balance |
| Ethanol | 3 |
| Glycerin | 4 |
| DPG | 9 |
| BG | 1 |
| PEG-6, PEG-32 | 3 |
| PEG/PPG-14/7dimethyl ether | 3 |
| PEG/polybutylene glycol-44/15 methyl ether hydrogenated dimer dilinoleyl | 0.4 |
| Ca chloride | 0.2 |
| Mg chloride | 0.1 |
| Na lactate | 0.4 |
| EDTA-2Na | 0.01 |
| Phenoxyethanol | 0.5 |
| Perfume | 0.01 |
| Total | 100 |

TABLE 9

| Ingredient | Content (%) |
| --- | --- |
| Water | Balance |
| Ethanol | 4 |
| Glycerin | 3 |
| DPG | 4 |
| Trehalose | 3 |
| PEG-8 | 1 |
| PEG/polybutylene glycol-44/15 methyl ether hydrogenated dimer dilinoleyl | 0.025 |
| Gellan gum | 0.2 |
| Xanthan gum | 0.04 |
| Citric acid | 0.01 |
| Na citrate | 0.09 |
| Phenoxyethanol | 0.3 |
| Methylparaben | 0.15 |
| Na metaphosphate | 0.01 |
| Perfume | 0.01 |
| Total | 100 |

When the first component (lotion) described in Table 8 and the second component (lotion) having a formula presented in Table 9 were paired, and respective mists of the first component and the second component were sprayed (in order), gelation took place on the skin, while providing excellent use feeling and moisturizing effect.

(Example 6)

A two-component cosmetic was prepared where Na alginate was used as a gel-forming substance to be contained in a second component and a divalent metal ion was used as a gel formation promoting substance to be contained in a first component.

Sample 1-1 (including calcium chloride and magnesium chloride) and Sample 1-2 (including no divalent metal) were prepared in each formulation presented in Table 10 below, and Sample 1-1 and Sample 1-2 were mixed in proper amounts to produce a variety of the first components having a different concentration of divalent metal ion.

Sample 2-1 (including Na alginate) and Sample 2-2 (including no Na alginate) were prepared in the same manner in each formulation presented in Table 11 below, and Sample 2-1 and Sample 2-2 were mixed in proper amounts to produce a variety of the second components having a different concentration of Na alginate.

TABLE 10

| Ingredient | Sample 1-1 | Sample 1-2 |
| --- | --- | --- |
| Ion exchanged water | 72.587 | 75.587 |
| Common alcohol 95% | 3 | 3 |
| Dynamite glycerin | 4 | 4 |
| Dipropylene glycol | 9 | 9 |
| 1,3-Butylene glycol | 1 | 1 |
| Polyethylene glycol 1500 | 3 | 3 |
| Polyoxyethylene (14) polyoxypropylene (7) dimethyl ether | 3 | 3 |
| Polyoxybutylene (15) polyoxyethylene (44) dimethyl dimer diol ether | 0.4 | 0.4 |
| Calcium chloride | 2 | — |
| Magnesium chloride | 1 | — |
| Sakihira mineral water | 0.1 | 0.1 |
| Lactic acid | 0.003 | 0.003 |
| Sodium lactate liquid (50%) | 0.4 | 0.4 |
| EDTA-2Na—2H2O | 0.01 | 0.01 |
| Phenoxyethanol | 0.3 | 0.3 |
| Methylparaben | 0.15 | 0.15 |
| Perfume | 0.05 | 0.05 |

TABLE 11

| | Sample 2-1 | Sample 2-2 |
| --- | --- | --- |
| Ion exchanged water | 81.7575 | 83.7575 |
| Common alcohol | 4 | 4 |
| Dynamite glycerin | 3 | 3 |
| Diglycerin | 0.5 | 0.5 |
| Dipropylene glycol | 4 | 4 |
| Trehalose | 3 | 3 |
| PEG-400 | 1 | 1 |
| Polyoxybutylene (15) polyoxyethylene (44) dimethyl dimer diol ether | 0.025 | 0.025 |
| Na alginate | 2 | — |
| Carboxymethylcellulose sodium | 0.05 | 0.05 |
| Sakihira mineral water | 0.1 | 0.1 |
| Citric acid (food) | 0.01 | 0.01 |
| Sodium citrate | 0.09 | 0.09 |
| Phenoxyethanol | 0.3 | 0.3 |
| Methylparaben | 0.15 | 0.15 |
| Sodium hexametaphosphate (first grade reagent) | 0.01 | 0.01 |
| Perfume | 0.0075 | 0.0075 |

When the concentration of each divalent metal cation included in the first component and the concentration of Na alginate included in the second component were changed, the occurrence of gelling and the appearance upon mixing of the first component and the second component were evaluated.

It was confirmed in the present Example that, when the concentration of each divalent metal cation in the first component was 0.1 to 5% by mass and the concentration of Na alginate in the second component was 0.1 to 5% by mass, gel formation was favorably made, and in particular, when the concentration of Na alginate was 0.3 to 2% by mass, gel further enhanced in uniformity was formed. On the other hand, when the concentration(s) of Na alginate and/or each divalent metal cation was/were more than 5% by mass, the problems of high stickiness and deterioration in use feeling were caused in some cases.

The invention claimed is:

1. A method for providing human skin with a barrier having an occlusive effect on moisture evaporation, comprising the ordered steps of:
   (1) applying to the skin a first component, which comprises a first substance consisting of a metal ion selected from the group consisting of $Na^+$, $K^+$, $Ca^{2+}$, $Mg^{2+}$ and $Al^{3+}$; and
   (2) applying to the skin, over the first component, a second component, which comprises a second substance consisting of a water-soluble polymer selected from the group consisting of soluble alginate and gellan gum;

whereby a barrier having an occlusive effect on moisture evaporation is formed on the skin.

2. The method of claim 1, wherein: the first substance is $Ca^{2+}$ or $Mg^{2+}$, and the second substance is a soluble alginate.

3. The method of claim 1, wherein: the first substance is $Ca^{2+}$ or $Mg^{2+}$, and the second substance is gellan gum.

* * * * *